US006533415B2

(12) United States Patent
Watanabe

(10) Patent No.: US 6,533,415 B2
(45) Date of Patent: Mar. 18, 2003

(54) OCULAR LENS MATERIAL HAVING HYDROPHILIC SURFACE AND PROCESS FOR PREPARING THE SAME

(75) Inventor: Tsuyoshi Watanabe, Kasugai (JP)

(73) Assignee: Menicon Co., Ltd., Nagoya (JP)

( * ) Notice: Subject to any disclaimer, the term of this patent is extended or adjusted under 35 U.S.C. 154(b) by 0 days.

(21) Appl. No.: 09/810,254

(22) Filed: Mar. 19, 2001

(65) Prior Publication Data
US 2001/0050749 A1 Dec. 13, 2001

(30) Foreign Application Priority Data

Mar. 21, 2000 (JP) ........................................ 2000-078322

(51) Int. Cl.$^7$ ................................................. G02C 7/04
(52) U.S. Cl. .................................. 351/160 H; 351/177
(58) Field of Search ........................ 351/160 R, 160 H, 351/161, 162, 177

(56) References Cited

U.S. PATENT DOCUMENTS 5,453,467 A    9/1995   Bamford et al.
5,648,442 A  * 7/1997   Bowers et al. ............... 526/277

FOREIGN PATENT DOCUMENTS

| EP | 0 574 352 A1 | 12/1993 |
| EP | 0 861 858 A2 | 9/1998 |
| EP | 0 818 479 B1 | 9/2000 |
| WO | WO 99/29750 | 6/1999 |
| WO | WO 99/57581 | 11/1999 |

* cited by examiner

Primary Examiner—Scott J. Sugarman
(74) Attorney, Agent, or Firm—Armstrong, Westerman & Hattori, LLP

(57) ABSTRACT

A process for preparing an ocular lens material having hydrophilic surface, characterized by comprising the steps of (1) irradiating the surface of an ocular lens material with high-frequency plasma or excimer ultarviolet-ray; (2) contacting the surface of the ocular lens material, which is treated in accordance with the step (1), with a hydrophilic monomer-mixture solution containing at least one zwitterionic group-containing compoud; and (3) irradiating the surface of the ocular lens material, which is in the state of contacting with the hydrophilic monomer-mixture solution in the step (2), with ultraviolet-ray having a wavelength of 250 to 500 nm and then, graft polymerizing the zwitterionic group-containing compound to the surface of the ocular lens material and then, forming a surface layer; and an ocular lens material having hydrophilic surface prepared by the process.

17 Claims, No Drawings

OCULAR LENS MATERIAL HAVING HYDROPHILIC SURFACE AND PROCESS FOR PREPARING THE SAME

BACKGROUND OF THE INVENTION

The present invention relates to an ocular lens material having hydrophilic surface and a process for preparing the same. In particular, the present invention relates to a process for easily preparing an ocular lens material having high oxygen permeability and is excellent in surface wettability to water, surface lubricity, water retention, deposit resistance and biocompatibility at the same time. More particularly, the present invention relates to an ocular lens material prepared by the above process, which has hydrophilic surface and the above excellent properties at the same time, and can be suitably used as an optical material including an ocular lens such as a contact lens, an intraocular lens or an artificial cornea, and a biocompatible material such as a medical material, a biochemical material, an engineering material or a pharmaceutical material.

In recent years, as to polymer materials, in particular, ocular lens materials, it is thought that one of the causes of various ocular diseases is lowering of hydrophilic property (wettability to tears) of the lens surface or adhering of deposit such as protein or lipid. So, to highten hydrophilic property and deposit resistance is watched.

Then, in order to improve hydrophilic property and adhering of deposit of the lens surface, which are the causes of various ocular diseases, modification of the surface of ocular lens materials has been examined.

As a method for modifying the surface of ocular lens materials, for instance, a method for improving wettability to water by plasma treatment for the surface of ocular lens materials (Japanese Examined Patent Publication No. 40293/1988) and a method for imparting hydrophilic property by graft polymerizing a hydrophilic monomer to the plasma-treated surface of ocular lens materials (Japanese Unexamined Patent Publication No. 49251/1994) have been proposed.

However, by the above methods, although hydrophilic property (wettability to tears) of the lens surface can be improved, deposit resistance of the lens cannot be sufficiently improved. In addition, biocompatibility of the obtained lens is insufficient.

The above graft polymerization method itself has been known in the field of polymer materials such as ocular lens materials. So, conventionally, various methods utilizing graft polymerization have been proposed.

For instance, a method comprising the steps of plasma irradiating a polymer substrate in the presence of inert gas, forming peroxide group on the surface of the polymer substrate by exposing the polymer substrate under an atmosphere of oxygen gas, and graft polymerizing various vinyl monomers to the peroxide group has been proposed (Japanese Unexamined Patent Publication No. 94819/1987, Japanese Unexamined Patent Publication No. 278224/1990, Japanese Unexamined Patent Publication No. 49251/1994, U.S. Pat. No. 5,805,264, Japanese Patent No. 2934965 and the like). Also, a graft polymerization method comprising a step of immersing an ocular lens material in a hydrophilic monomer solution containing an aqueous peroxides has been proposed (Japanese Unexamined Patent Publication No. 10055/2000). In accordance with these methods, graft polymerization of various monomers to the material surface can be carried out. However, in general, energy for initiating graft polymerization is thermally imparted.

When thermal graft polymerization method is employed, longer period of time for polymerization is needed. So, it is desired to shorten polymerization time. When polymerization is carried out for a long period of time, introduction of polymer chains to the inside of material is accelerated. As a result, deformation of an ocular lens material occurs. Furthermore, because it is difficult to control polymerization degree during thermal polymerization for a long period of time, the thermal polymerization method is unsuitable for preparing a uniform treated layer.

On the other hand, it is thought that introduction of a vinyl monomer having a zwitterionic group which can impart excellent water retention, deposit resistance and biocompatibility to the polymer surface is one of effective ways.

For instance, a method for graft polymerizing a monomer having a zwitterionic group to the surface of hydrogel has been proposed (U.S. Pat. No. 5,453,467). However, because thermal graft polymerization is carried out in this method, the method has the same problem as above. So, it is desired to dissolve the problem. Also, because the above hydrogel has no silicone-containing component, it is difficult to prepare an ocular lens material having high oxygen permeability.

Then, a method for graft polymerizing a monomer having a zwitterionic group to the activated surface of an ocular lens material prepared by using a silicone-containing component has been proposed (Japanese Unexamined Patent Publication No. 122779/1994 and Japanese Unexamined Patent Publication No. 72430/1995). However, because thermal graft polymerization is carried out in this method, the method has the same problem as above.

A graft polymerization method with a microwave having a wavelength of 250 to 500 nm has been proposed (Japanese Unexamined Patent Publication No. 60142/1998). However, because no monomer having a zwitterionic group is used in graft polymerization, a hydrophilic membrane formed by the method cannot impart sufficient water retention and biocompatibility.

A method for graft polymerizing a monomer having a zwitterionic group at hydroxyl group on the material surface as the initiation point by using a transition metal salt has been proposed (Japanese Unexamined Patent Publication No. 510322/1994). However, it is difficult to remove an initiator such as the transition metal salt in this method. Also, because thermal graft polymerization is carried out in this method, the method has the same problem as above.

A method for imparting hydrophilic property, comprising steps of immersing an ocular lens material in a hydrophilic monomer solution and irradiating the ocular lens material with ultraviolet-ray has been proposed (Japanese Unexamined Patent Publication No. 10054/2000). However, in the case that the ocular lens material is hydrogel, hydrophilic polymer chains are introduced to the inside of the hydrogel, so that optical property becomes bad. Also, it becomes difficult to remove the hydrophilic polymer chains from the inside of the hydrogel. In addition, in the case that the ocular lens material is a hard material, there is a problem that it is difficult to introduce the hydrophilic polymer chains to the hard material because it is very difficult to graft polymerize the hydrophilic monomers to the surface of the hard material.

In recent years, as a method for controlling molecular weight and molecular weight distribution during radical polymerization, a method comprising a step of adding a sulfur-containing compound as a chain transfer agent to a polymerization system has been reported (John Chiefari et.

al., Macromolecules, 31, p5559 (1999)). Furthermore, a surface graft polymerization method using the above chain transfer agent has been reported (Tsujii Yoshinobu et. al., Polymer Preprints, Japan, 49, p1129 (2000)). In accordance with these methods, molecular weight and molecular weight distribution in the aimed polymer can be controlled by utilizing the chain transfer agent in polymerization. However, to control of molecular weight and molecular weight distribution in the polymer and to impart of hydrophilic property to the polymer surface have not been carried out at the same time. So, technical development has been desired.

On the other hand, as one of methods for introducing a monomer having a zwitterionic group to a silicone hydrogel, a method for forming inter-penetrating polymer network structure (in general, referred to as IPN structure) composed of a silicone segment and a hydrophilic segment has been proposed (International Publication No. WO99/29750). However, when the method is employed, the aimed material sometimes deforms. Accordingly, the method is unsuitable for preparing an optical material.

As mentioned above, when conventional various methods are employed, it is difficult to easily prepare an ocular lens material for a relatively short period of time, which has various properties desired in recent years. Accordingly, development of excellent methods in spite of the conventional methods has been expected.

An object of the present invention is to provide a process for easily preparing an ocular lens material having high oxygen permeability and is excellent in surface wettability to water, surface lubricity, water retention, deposit resistance and biocompatibility at the same time.

The other object of the present invention is to provide an ocular lens material prepared by the above process.

These and other objects of the present invention will become apparent from the description hereinafter.

SUMMARY OF THE INVENTION

In accordance with the present invention, there is provided
(A) a process for preparing an ocular lens material having hydrophilic surface, characterized by comprising the steps of
(1) irradiating the surface of an ocular lens material with high-frequency plasma or excimer ultraviolet-ray;
(2) contacting the surface of the ocular lens material, which is treated in accordance with the step (1), with a hydrophilic monomer-mixture solution containing at least one zwitterionic group-containing compoud; and
(3) irradiating the surface of the ocular lens material, which is in the state of contacting with the hydrophilic monomer-mixture solution in the step (2), with ultraviolet-ray having a wavelength of 250 to 500 nm and then, graft polymerizing the zwitterionic group-containing compound to the surface of the ocular lens material and then, forming a surface layer; and
(B) an ocular lens material prepared by the above process.

DETAILED DESCRIPTION

In the process of the present invention, at first, the surface of an ocular lens material is irradiated with high-frequency plasma or excimer ultraviolet-ray (Step (1)).

In the above Step (1), by irradiation with high-frequency plasma or excimer ultraviolet-ray, a radical generates on a surface layer of the ocular lens material.

The irradiation with high-frequency plasma is carried out, for instance, under an atmosphere of oxygen gas, under an atmosphere of inert gas or in the air, preferably under an atmosphere of oxygen gas or in the air. That is, the ocular lens material is put under an atmosphere of oxygen gas, under an atmosphere of inert gas or in the air in a plasma state. Preferably, the ocular lens material is put under an atmosphere of oxygen gas in a plasma state, or under atmospheric pressure in a steady state and not in a plasma state, for about 0.5 to 30 minutes. As a result, a radical generates on the surface of the ocular lens material. The plasma state between electrodes in a plasma generator may be under reduced pressure such as 1.3 to $1.3 \times 10^2$ Pa or so, or may be under ordinary pressure.

The irradiation with excimer ultraviolet-ray is preferably carried out by irradiating the ocular lens material with vacuum ultraviolet-ray having a wavelength of 172 nm for 0.5 to 60 minutes or so. As a result, a radical generates on the surface of the ocular lens material.

After the radical generates on the surface of the ocular lens material by irradiation with high-frequency plasma or excimer ultraviolet-ray, the ocular lens material is contacted with the air or oxygen for 1 to 120 minutes or so, so that a peroxide (peroxide group) is formed on the surface of the material.

The ocular lens material used in the present invention is not particularly limited. For instance, the ocular lens material may be a non-water-containing rigid material or a water-containing hydrogel.

As the ocular lens material, a copolymer prepared by polymerizing a monomer mixture in accordance with a conventional method can be used. For instance, in the monomer mixture are contained a silicon-containing monomer such as a silicon-containing alkyl (meth)acrylate, a silicon-containing styrene derivative or a polysiloxane macromonomer; a fluorine-containing monomer such as a fluorine-containing alkyl (meth)acrylate; a hydrophilic monomer such as a hydroxyl group-containing alkyl (meth)acrylate, a dialkyl(meth)acrylamide, (meth)acrylic acid or a N-vinyllactam; a monomer for adjusting hardness of the material, such as an alkyl (meth)acrylate, styrene, an α-methylstyrene or an alkyl-α-methylstyrene; and a crosslinkable monomer having at least 2 polymerizable unsaturated double bonds. In particular, in consideration of oxygen permeability and deposit resistance of the material itself, an ocular lens material comprising a copolymer prepared by polymerizing a monomer mixture containing at least one selected from the silicon-containing monomer and the fluorine-containing monomer is preferably used.

In the present specification, "—(meth)acrylate" means "—acrylate and/or methacrylate", and the same is also true for the other (meth)acrylate derivatives.

Then, the surface of the ocular lens material, which is treated in accordance with the Step (1), is contacted with a hydrophilic monomer-mixture solution containing at least one zwitterionic group-containing compound (Step (2)).

A method for contacting the surface of the ocular lens material with the hydrophilic monomer-mixture solution is not particularly limited. In order to sufficiently contact the surface with the hydrophilic monomer-mixture solution, it is desired that the ocular lens material is immersed in the hydrophilic monomer-mixture solution.

The time for contacting the surface of the ocular lens material with the hydrophilic monomer-mixture solution is also not particularly limited. It is desired that the surface is sufficiently contacted with the hydrophilic monomer-mixture solution. As usual, it is desired that the surface of the ocular lens material is irradiated with ultraviolet-ray during the aforementioned step as the surface is contacted with the hydrophilic monomer-mixture solution.

As mentioned above, the hydrophilic monomer-mixture solution used in the Step (2) contains at least one zwitterionic group-containing compound.

The zwitterionic group-containing compound is a compound having not only the center of permanent positive charge but also the center of negative charge in its structure. Typical examples of the zwitterionic group-containing compound are, for instance, a compound (I) represented by the formula (I):

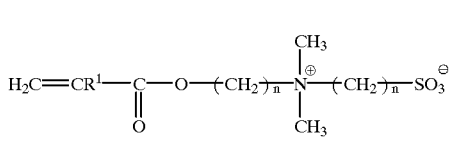

(I)

wherein $R^1$ is hydrogen atom or methyl group, and n is an integer of 1 to 10;
a compound (II) represented by the formula (II):

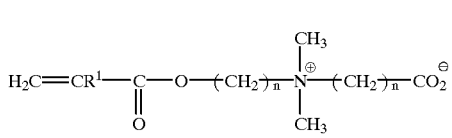

(II)

wherein $R^1$ is hydrogen atom or methyl group, and n is an integer of 1 to 10;
a compound (III) represented by the formula (III):

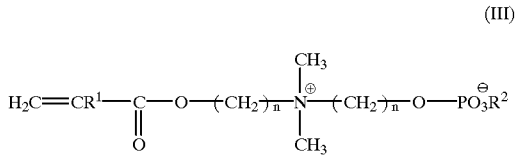

(III)

wherein $R^1$ is hydrogen atom or methyl group, $R^2$ is a hydrocarbon group having 1 to 6 carbon atoms, and n is an integer of 1 to 10;
a compound (IV) represented by the formula (IV):

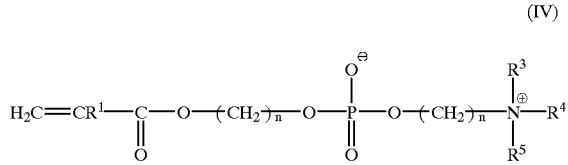

(IV)

wherein $R^1$ is hydrogen atom or methyl group, each of $R^3$, $R^4$ and $R^5$ is independently a hydrocarbon group having 1 or 2 carbon atoms, and n is an integer of 1 to 10;
and the like. These can be used alone or in admixture thereof.

Concrete examples of the compound (I) are, for instance, dimethyl(3-sulfopropyl)(2-(meth)acryloyloxyethyl) ammonium betaine and the like.

Concrete examples of the compound (II) are, for instance, dimethyl(2-carboxyethyl) (2-(meth) acryloyloxyethyl) ammonium betaine and the like.

Concrete examples of the compound (III) are, for instance, dimethyl(3-methoxyphosphopropyl)(2-(meth)acryloyloxyethyl) ammonium betaine and the like.

Concrete examples of the compound (IV) are, for instance, 2-(meth)acryloyloxyethyl phosphorylcholine and the like.

Among them, because graft polymerizability to the surface of the ocular lens material is more excellent, dimethyl (3-sulfopropyl)(2-(meth)acryloyloxyethyl) ammonium betaine and 2-(meth)acryloyloxyethyl phosphorylcholine are particularly preferable.

The amount of the zwitterionic group-containing compound in the hydrophilic monomer-mixture solution should be defined in sufficient consideration of forming a uniform surface layer (treated layer) on the surface of the ocular lens material. In order to sufficiently exhibit effect for improving hydrophilic property (surface wettability to water) and surface lubricity of the finally aimed ocular lens material having hydrophilic surface and effect for restraining adhesion of lipid and protein, it is desired that the amount of the zwitterionic group-containing compound in the hydrophilic monomer-mixture solution is at least 0.01 mol/L, preferably at least 0.05 mol/L, more preferably at least 0.1 mol/L. In order to remove fears that it becomes difficult to remove non-reacted residual compounds from the ocular lens material after graft polymerization and that optical property of the ocular lens material becomes bad because polymer chains are introduced to the inside of the ocular lens material due to too increase of graft polymerization degree, it is desired that the amount of the zwitterionic group-containing compound in the hydrophilic monomer-mixture solution is at most 40 mol/L, preferably at most 20 mol/L, more preferably at most 10 mol/L.

The hydrophilic monomer-mixture solution can suitably contain at least one of a hydrophilic monomer other than the zwitterionic group-containing compound, a crosslinkable monomer, water and an organic solvent in addition to the zwitterionic group-containing compound. For instance, in particular, it is preferable that the hydrophilic monomer-mixture solution essentially contains water and the organic solvent, and further contains at least one selected from the hydrophilic monomer other than the zwitterionic group-containing compound and the crosslinkable monomer.

Typical examples of the hydrophilic monomer other than the zwitterionic group-containing compound are, for instance, an alkyl(meth)acrylamide such as N,N-dimethyl (meth)acrylamide, N,N-diethyl(meth)acrylamide, N,N-dipropyl(meth)acrylamide or N-isopropyl(meth)acrylamide; N-vinylformamide; N-vinylacetamide; acryloylmorpholine; a N-vinyllactam such as N-vinyl-2-pyrrolidone, N-vinylpiperidone, N-vinylcaprolactam, N-vinylcaprylolactam or N-(meth)acryloyloxyethyl-2-pyrrolidone; a hydroxyalkyl (meth)acrylate such as 2-hydroxyethyl (meth)acrylate, 2-hydroxypropyl (meth) acrylate or 2-hydroxybutyl (meth)acrylate; (meth)acrylic acid; a polyalkylene glycol mono(meth)acrylate such as polyethylene glycol mono(meth)acrylate or polypropylene glycol mono(meth)acrylate; and the like. These can be used alone or in admixture thereof.

When the hydrophilic monomer-mixture solution contains the hydrophilic monomer other than the zwitterionic group-containing compound, in order to improve copolymerizability of the hydrophilic monomer with the zwitterionic group-containing compound and to effectively introduce the hydrophilic monomer to the inside of graft chains, it is desired that the amount of the hydrophilic monomer in the hydrophilic monomer-mixture solution is at least 0.01 mol/L, preferably at least 0.05 mol/L, more preferably at least 0.1 mol/L. In order to effectively exhibit properties of the zwitterionic group-containing compound, it is desired that the amount of the hydrophilic monomer in the hydrophilic monomer-mixture solution is at most 40 mol/L, preferably at most 20 mol/L, more preferably at most 10 mol/L.

As the crosslinkable monomer, a monomer having at least 2 polymerizable unsaturated double bonds can be used. Typical examples of the crosslinkable monomer are, for instance, ethylene glycol di(meth)acrylate, diethylene glycol di(meth)acrylate, triethylene glycol di(meth)acrylate, tetraethylene glycol di(meth)acrylate, polyethylene glycol di(meth)acrylate, ethylene glycol diallyl ether, diethylene glycol diallyl ether, triethylene glycol diallyl ether, tetraethylene glycol diallyl ether, polyethylene glycol diallyl ether, methylenebis(meth)acrylamide, divinylbenzene, vinylbenzyl (meth)acrylate, allyl (meth)acrylate, vinyl (meth)acrylate and the like. These can be used alone or in admixture thereof. Among them, for instance, in consideration of the use of the aforementioned water as a solvent, it is preferable that the hydrophilic monomer-mixture solution contains an aqueous crosslinkable monomer.

In order to effectively fulfill functions of graft-treated layers and graft chains by controlling graft density, it is desired that the amount of the crosslinkable monomer in the hydrophilic monomer-mixture solution is at least 0.01 part by weight, preferably at least 0.05 part by weight, more preferably at least 0.1 part by weight, based on 100 parts by weight of the total amount of the zwitterionic group-containing compound and the hydrophilic monomer other than the zwitterionic group-containing compound, or 100 parts by weight of the zwitterionic group-containing compound. In order not to restrict mobility of graft chains and to keep the shape of the ocular lens material, it is desired that the amount of the crosslinkable monomer in the hydrophilic monomer-mixture solution is at most 20 parts by weight, preferably at most 10 parts by weight, more preferably at most 5 parts by weight, based on 100 parts by weight of the total amount of the zwitterionic group-containing compound and the hydrophilic monomer other than the zwitterionic group-containing compound, or 100 parts by weight of the zwitterionic group-containing compound.

The zwitterionic group-containing compound, and as occasion demands, the hydrophilic monomer other than the zwitterionic group-containing compound and the crosslinkable monomer in the hydrophilic monomer-mixture solution are graft polymerized preferably by using water and an organic solvent.

Typical examples of the organic solvent are, for instance, an alcohol such as methanol or ethanol, acetone, tetrahydrofuran, N,N-dimethylformamide, hexane, benzene, toluene, acetonitrile, methylene chloride and the like. These can be used alone or in admixture thereof, Because removal from the ocular lens material after graft polymerization is easy, it is preferable that water is used.

The amount of water and/or the organic solvent in the hydrophilic monomer-mixture solution is suitably adjusted so that the amount of each of the zwitterionic group-containing compound, the hydrophilic monomer other than the zwitterionic group-containing compound and the crosslinkable monomer in the hydrophilic monomer-mixture solution is included in the above range.

When the hydrophilic monomer-mixture solution contains water and the organic solvent, and also contains at least one selected from the hydrophilic monomer other than the zwitterionic group-containing compound and the crosslinkable monomer, during graft polymerization in the aforementioned Step (3), in order to uniformly and minutely control polymerization degree and molecular weight distribution, it is preferable that the hydrophilic monomer-mixture solution further contains a chain transfer agent represented by the formula (V):

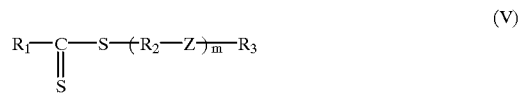

wherein $R^1$ is hydrogen atom, a linear, branched or cyclic aliphatic hydrocarbon group having 1 to 12 carbon atoms, or a linear or branched aliphatic hydrocarbon group having 6 to 24 carbon atoms and containing aromatic hydrocarbon group having 6 to 12 carbon atoms; $R_2$ is a linear, branched or cyclic aliphatic hydrocarbon group having 1 to 12 carbon atoms; $R_3$ is hydrogen atom, a linear, branched or cyclic aliphatic hydrocarbon group having 1 to 12 carbon atoms, a linear or branched aliphatic hydrocarbon group having 6 to 24 carbon atoms and containing aromatic hydrocarbon group having 6 to 12 carbon atoms, or cyano group; Z is oxygen atom, —COO— group, —OOC— group, —(CH$_2$CH$_2$O)$_1$— group (in which 1 is an integer of 1 to 12), or direct bond; and m is 0 or an integer of 1 to 10.

In particular, typical examples of the chain transfer agent are, for instance, benzyl thiobenzoate, 1-phenylethyl dithiobenzoate, 2-phenyl-2-propinyl dithiobenzoate, 1-acetoxyethyl dithiobenzoate, benzyl dithioacetate, t-butyl dithiobenzoate, 2-cyano-2-propinyl dithiobenzoate and the like. These can be used alone or in admixture thereof.

In order to uniformly and minutely control polymerization degree and molecular weight distribution, it is desired that the amount of the chain transfer agent in the hydrophilic monomer-mixture solution is at least 0.001 part by mole, preferably at least 0.01 part by mole, more preferably at least 0.05 part by mole, based on 100 parts by mole of the total amount of monomers for graft polymerization. From the viewpoints that graft polymerization chain needs suitable length for imparting hydrophilic property to the ocular lens material and the length of graft polymerization chain becomes short due to the excessive amount of the chain transfer agent, it is desired that the amount of the chain transfer agent in the hydrophilic monomer-mixture solution is at most 20 parts by mole, preferably at most 10 parts by mole, more preferably at most 5 parts by mole, based on 100 parts by mole of the total amount of monomers for graft polymerization.

When the chain transfer agent is used, polymerization reaction system is contacted with oxygen during the latter of graft polymerization in the aforementioned Step (3), and introduction of a terminal group derived from the chain transfer agent into a polymer chain terminal can be prevented. When a residual group on the polymer chain terminal derived from the chain transfer agent generates after graft polymerization in Step (3), it is preferable that the residual group is removed or converted.

The residual group on the polymer chain terminal derived from the chain transfer agent, which generates after graft polymerization, can be removed or converted by reacting with a sulfur-containing compound such as 2-mercapto ethanol or 2-mercapto propionic acid, or reacting with an alkyl alcohol such as methanol or ethanol in the presence of an acid or an alkali.

Then, the surface of the ocular lens material, which is in the state of contacting with the hydrophilic monomer-mixture solution in the Step (2), is irradiated with ultraviolet-ray having a wavelength of 250 to 500 nm, and the zwitterionic group-containing compound is graft polymerized to the surface of the ocular lens material, so that a surface layer is formed (Step (3)).

The graft polymerization starts by irradiating the surface of the ocular lens material, which is in the state of contacting with the hydrophilic monomer-mixture solution in the Step (2), with ultraviolet-ray. Then, the polymerization reaction uniformly proceeds and is finished.

In order to sufficiently exhibit effect for improving hydrophilic property (surface wettability to water), surface lubricity and water retention of the finally aimed ocular lens material having hydrophilic surface and effect for restraining adhesion of lipid and protein, it is desired that illuminance of ultraviolet-ray is at least 0.1 mW/cm$^2$, preferably at least 0.5 mW/cm$^2$. In order to remove a fear of deterioration of the ocular lens material itself, it is desired that illuminance of ultraviolet-ray is at most 20 mW/cm$^2$, preferably at most 15mW/cm$^2$.

In order to sufficiently exhibit effect for improving hydrophilic property (surface wettability to water), surface lubricity and water retention of the finally aimed ocular lens material having hydrophilic surface and effect for restraining adhesion of lipid and protein, it is desired that irradiation time with ultraviolet-ray, that is graft polymerization reaction time, is at least 1 second, preferably at least 1 minute. In order to remove fears that the ocular lens material, for instance, which is hydrogel, deforms after irradiation with ultraviolet-ray due to too increase of graft polymerization degree and that function as an optical lens material is lost due to lowering of transparency, it is desired that irradiation time with ultraviolet-ray, that is graft polymerization reaction time, is at most 24 hours, preferably at most 60 minutes.

In order to sufficiently exhibit effect for improving hydrophilic property (surface wettability to water) and surface lubricity of the finally aimed ocular lens material having hydrophilic surface and effect for restraining adhesion of lipid and protein, it is desired that reaction temperature during graft polymerization is at least 0° C., preferably at least 15° C. In order to remove fears that the ocular lens material, for instance, which is hydrogel, deforms after irradiation with ultraviolet-ray due to too increase of graft polymerization degree and that function as an optical lens material is lost due to lowering of transparency, it is desired that reaction temperature during graft polymerization is at most 120° C., preferably at most 90° C.

When the hydrophilic monomer-mixture solution contains solvents such as water and the organic solvent, the hydrophilic monomer-mixture solution is sufficiently stirred or shaken, so that the reaction uniformly proceeds.

On the surface of the ocular lens material treated in accordance with the above Step (3), a surface layer (treated layer) in which polymerization degree is preferably controlled and of which the depth is uniformly limited for several one hundred angstrom can be formed. Accordingly, possibility of losing characteristics and properties of bulk is extremely low.

The ocular lens material having hydrophilic surface can be prepared in accordance with the above Step (1), Step (2) and Step (3). It is preferable that a non-reacted residual component is removed with at least one selected from water and an organic solvent from the surface layer of the ocular lens material, which is formed in the Step (3) (Step (4)).

As the organic solvent used in the Step (4), a solvent which can dissolve the non-reacted residual component such as the zwitterionic group-containing compound, the hydrophilic monomer other than the zwitterionic group-containing compound or the crosslinkable monomer, which is contained in the surface layer of the ocular lens material, may be used. Examples of the organic solvent are, for instance, ethanol, acetone, tetrahydrofuran, acetonitrile, methylene chloride and the like. Removal of the non-reacted residual component may be carried out by extraction for suitable time in accordance with Soxhlet extraction method. After extraction by using the organic solvent, as occasion demands, the ocular lens material is boiled in water or physiological saline.

According to the process of the present invention, the ocular lens material which has high oxygen permeability and is excellent in surface wettability to water, surface lubricity, water retention, deposit resistance and biocompatibility at the same time can be easily prepared.

Accordingly, the ocular lens material having hydrophilic surface and the above excellent properties at the same time can be suitably used as an optical material including an ocular lens such as a contact lens, an intraocular lens or an artificial cornea, and a biocompatible material such as a medical material, a biochemical material, an engineering material or a pharmaceutical material.

The ocular lens material having hydrophilic surface and the process for preparing the same of the present invention are more specifically described and explained by mans of the following Examples. It is to be understood that the present invention is not limited to the Examples, and various changes and modifications may be made in the invention without departing from the spirit and scope thereof.

EXAMPLE 1

[Graft Polymerization to Silicone Hydrogel]

As a monomer mixture, 30 parts by weight of urethane bond-containing polysiloxane macromonomer represented by the formula:

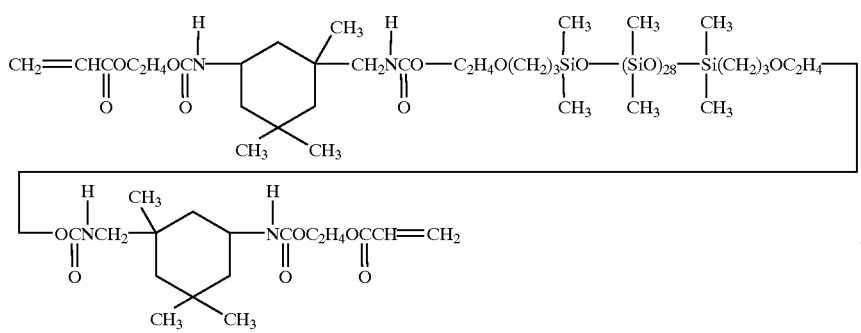

30 parts by weight of tris(trimethylsiloxysilyl)propyl methacrylate, 10 parts by weight of N,N-dimethylacrylamide, 30 parts by weight of N-vinyl-2-pyrrolidone and 0.3 part by weight of ethylene glycol dimethacrylate (hereinafter referred to as "EDMA") were used. The monomer mixture was polymerized in accordance with a usual polymerization method to give a copolymer. Then, a contact lens (diameter: 13.0 mm, thickness: 0.08 mm (wetting state)) and a plate (diameter: 15.0 mm, thickness: 0.2 mm (wetting state)) were made of the copolymer. The contact lens and the plate were set in a discharge apparatus (made by Kyoto Denshi-Keisoku Co., Ltd., low temperature ashing apparatus PA-102AT). After the pressure in a chamber of the discharge apparatus was reduced to about 2.66 Pa, plasma discharge treatment was carried out for 10 minutes under an atmosphere of oxygen gas of about 13.3 Pa (frequency: 13.56 MHz, high frequency power: 50 W). After that, the contact lens and the plate were stored for at least 10 minutes under an atmosphere of oxygen gas. As a result, peroxides (peroxide groups) generated on the surface of the contact lens and the surface of the plate.

Then, as the hydrophilic monomer-mixture solution, 3.0 mol/L aqueous solution of dimethyl(3-sulfopropyl)(2-methacryloyloxyethyl) a ammonium betaine (hereinafter referred to as "SAMA") was prepared. The contact lens and the plate were immersed in this aqueous solution, and were aerated with nitrogen gas. The contact lens and the plate in the state of immersing in the aqueous solution were irradiated with ultraviolet-ray (wavelength: 360 nm) at an illuminance of 1.5 mW/cm$^2$ at room temperature for 10 minutes, and graft polymerization was carried out. After graft polymerization was finished, the contact lens and the plate were picked up from the aqueous solution and washed in distilled water. Furthermore, the contact lens and the plate were extracted with distilled water by using Soxhlet's extractor for 16 hours. As a result, non-reacted residual components were removed from the surface of the contact lens and the surface of the plate.

Then, the contact lens and the plate were hydrated with physiological saline to give hydrated silicone hydrogels as test pieces. Transparency, surface wettability to water, surface lubricity, water content, refractive index, oxygen permeability, adhesion resistance of lipid and protein, graft weight, contact angle and water retention of the test pieces were examined in accordance with the following methods, and elemental analysis of the test piece (plate) was carried out in accordance with the following method. The results are shown in TABLE 1 and TABLE 2.

(1) Transparency

The test piece (contact lens) in water was observed with naked eyes and transparency of the test piece was evaluated based on the following criteria for evaluation.
(Criteria for Evaluation)
○: Transparent
Δ: Slightly opaque
×: Extremely opaque (2) Surface Wettability to Water The surface of the test piece (contact lens) picked up from physiological saline after hydration was observed with naked eyes and surface wettability to water of the test piece was evaluated based on the following criteria for evaluation.
(Criteria for Evaluation)
○: Non-water repellent and uniformly wet
Δ: Slightly water repellent
×: Extremely water repellent (3) Surface Lubricity The test piece (contact lens) was touched with fingers, and lubricity of the surface of the test piece was examined. Then, surface lubricity of the test piece was evaluated based on the following criteria for evaluation.
(Criteria for Evaluation)
○: Excellent in lubricity
Δ: Frictional feeling
×: Extremely sticky (4) Water Content The weight of the test piece (plate) in the equilibrium water-containing state after hydration ($W_1$ (g)) was measured. Also, the weight of the test piece in the dry state after drying of the water-containing test piece in an oven ($W_0$ (g)) was measured. Using the values of $W_1$ and $W_0$, water content (% by weight) of the test piece was calculated in accordance with the following equation.

$$\text{Water content (\% by weight)} = \{(W_1 - W_0)/W_1\} \times 100$$

(5) Refractive Index

Using refractive index meter (made by Atago Co., Ltd., 1T), refractive index (no unit) of the test piece (plate) was measured at 25° C. under the relative humidity of 50%.

(6) Oxygen Permeability ($Dk_{O_2}$)

Using Seikaken-type film oxygen-gas permeator (made by RIKASEIKI KOGYO CO., LTD.), oxygen permeability of the test piece (plate) was measured in physiological saline at 35° C. The unit of oxygen permeability is (cm$^2$/sec)(mLO$_2$/(mL×hPa)), and the numerical value shown in TABLE 1 and TABLE 2 was obtained by multiplying the measured value of the test piece by $10^{11}$ times.

(7) Adhesion Resistance of Lipid and Protein (i) Adhesion Resistance of Lipid

The test piece (plate) was immersed in an artificial ocular lipid solution (lipid concentration: 5.0 mg/mL) and was shaken at 37° C. for 5 hours. Then, the artificial ocular lipid solution was extracted with ethanol/diethyl ether mixture solution (volume ratio: ethanol/diethyl ether=3/1) for 10 minutes. The amount of lipid in an extract was quantified in accordance with Sulfo-Phospho-Vanillin method and the adhering lipid amount (mg/cm$^2$) per 1 cm$^2$ of the test piece was obtained.

(ii) Adhesion Resistance of Protein

The test piece (plate) was immersed in FDA artificial tear solution (protein concentration: 6.69 mg/mL) and was shaken at 37° C. for 5 hours. Then, the artificial tear solution was extracted with 1% sodium dodecylsulfate (SDS) solution at 37° C. for 3 hours. The amount of protein in an extract was quantified in accordance with bicinchoninic acid method and the adhering protein amount ($\mu$g/cm$^2$) per 1 cm$^2$ of the test piece was obtained.

(8) Graft Weight

The weight of the plate in the dry state before graft polymerization reaction ($W_0$ (mg)) was previously measured. Then, the plate after finishing graft polymerization reaction was dried in an oven at 105° C. for at least 16 hours, the weight of the plate ($W_2$ (mg)) was measured. Using the values of $W_0$ and $W_2$, and the surface area of the plate (S (mm$^2$)), graft weight (mg/mm$^2$) per 1 mm$^2$ of the plate was calculated in accordance with the following equation.

$$\text{Graft weight } (mg/mm^2) = (W_2 - W_0)/S$$

(9) Contact Angle

Using goniometer (made by ERMA INC., G-1, 2MG), contact angle (°) of the test piece (plate) was measured in physiological saline at 25° C. in accordance with bubbling method. Through a syringe, 2 μL of bubble adhered to the test piece immersed in physiological saline. Then, the contact angle shown in TABLE 1 and TABLE 2 was obtained by averaging left contact angle and right contact angle, between the test piece and bubble.

(10) Water Retention

The weight of the test piece (contact lens) in the equilibrium water-containing state after hydration ($W_0$ (g)) was measured. After the test piece was stayed as it were at 25° C. under the relative humidity of 50% for 15 minutes, the weight of the test piece ($W_3$ (g)) was measured. Using the values of $W_3$ and $W_0$, and water content (WC (% by weight)) calculated in the above item (4), water retention (% by weight) of the test piece was calculated in accordance with the following equation.

Water retention (% by weight) = $100 - \{[(W_0-W_3)/W_0 \times 100]/WC \times 100\}$

(11) Elemental Analysis (Dry State)

The test piece (plate) was dried in an oven at 105° C. for at least 16 hours, and elemental analysis of the surface of the test piece was carried out by X-ray photoelectron spectroscopy apparatus (made by JEOL LTD., JPS-9000MX).

EXAMPLE 2

Test pieces were produced in the same manner as in EXAMPLE 1 except that as the hydrophilic monomer-mixture solution, 0.5 mol/L aqueous solution of SAMA, containing tetraethylene glycol diacrylate in an amount of 1.0 part by weight based on 100 parts by weight of SAMA, was used instead of the 3.0 mol/L aqueous solution of SAMA used in EXAMPLE 1. Properties of the test pieces were examined in the same manner as in EXAMPLE 1, and elemental analysis of the test piece (plate) was carried out in the same manner as in EXAMPLE 1. The results are shown in TABLE 1 and TABLE 2.

EXAMPLE 3

Test pieces were produced in the same manner as in EXAMPLE 1 except that condition for plasma discharge treatment was changed from 10 minutes under an atmosphere of oxygen gas in EXAMPLE 1 to 2 minutes under an atmosphere of oxygen gas, and that as the hydrophilic monomer-mixture solution, 0.5 mol/L aqueous solution of SAMA, containing tetraethylene glycol dimethacrylate in an amount of 2.0 parts by weight based on 100 parts by weight of SAMA, was used instead of the 3.0 mol/L aqueous solution of SAMA used in EXAMPLE 1. Properties of the test pieces were examined in the same manner as in EXAMPLE 1, and elemental analysis of the test piece (plate) was carried out in the same manner as in EXAMPLE 1. The results are shown in TABLE 1 and TABLE 2.

EXAMPLE 4
[Graft Polymerization to Silicone Hydrogel]

The same contact lens and the same plate as in EXAMPLE 1 were irradiated with excimer vacuum ultraviolet-ray (wavelength: 172 nm) by an irradiation apparatus (made by USHIO INC.) for 10 minutes. After that, the contact lens and the plate were stored for at least 10 minutes under an atmosphere of oxygen gas. As a result, peroxides (peroxide groups) generated on the surface of the contact lens and the surface of the plate.

Then, as the hydrophilic monomer-mixture solution, 0.5 mol/L aqueous solution of SAMA was prepared. The contact lens and the plate were immersed in this aqueous solution, and were aerated with nitrogen gas. The contact lens and the plate in the state of immersing in the aqueous solution were irradiated with ultraviolet-ray (wavelength: 360 nm) at an illuminance of 1.5 mW/cm$^2$ at room temperature for 10 minutes, and graft polymerization was carried out. After graft polymerization was finished, the contact lens and the plate were picked up from the aqueous solution and washed in distilled water. Furthermore, the contact lens and the plate were extracted with distilled water by using Soxhlet's extractor for 16 hours. As a result, non-reacted residual components were removed from the surface of the contact lens and the surface of the plate.

Then, the contact lens and the plate were hydrated with physiological saline to give hydrated silicone hydrogels as test pieces. Properties of the test pieces were examined in the same manner as in EXAMPLE 1, and elemental analysis of the test piece (plate) was carried out in the same manner as in EXAMPLE 1. The results are shown in TABLE 1 and TABLE 2.

EXAMPLE 5

Test pieces were produced in the same manner as in EXAMPLE 4 except that as the hydrophilic monomer-mixture solution, 0.5 mol/L aqueous solution of 2-(methacryloyloxyethyl) phosphorylcholine was used instead of the 0.5 mol/L aqueous solution of SAMA used in EXAMPLE 4. Properties of the test pieces were examined in the same manner as in EXAMPLE 1, and elemental analysis of the test piece (plate) was carried out in the same manner as in EXAMPLE 1. The results are shown in TABLE 1 and TABLE 2.

EXAMPLE 6
[Graft Polymerization to Silicone Hydrogel Using Chain Transfer Agent]

A contact lens (diameter: 13.0 mm, thickness: 0.08 mm (wetting state)) and a plate (diameter: 15.0 mm, thickness: 0.2 mm (wetting state)) were made of the same copolymer as in EXAMPLE 1. By using a discharge apparatus (made by Keyence Co., Ltd., ST-7000), plasma discharge treatment was carried out to the contact lens and the plate for 1 minute under atmospheric pressure (work distance: 6 mm, voltage: 10 kV, frequency: 20 to 25 kHz, gas: air). After that, the contact lens and the plate were stored for at least 10 minutes under an atmosphere of oxygen gas. As a result, peroxides (peroxide groups) generated on the surface of the contact lens and the surface of the plate.

Then, as the hydrophilic monomer-mixture solution, 0.5 mol/L aqueous solution of SAMA (containing methanol in an amount of 5 parts by weight based on 100 parts by weight of water), containing benzyl thiobenzoate as the chain transfer agent in an amount of 0.1 part by mole based on 100 parts by mole of SAMA, was prepared. The contact lens and the plate were immersed in this aqueous solution, and were aerated with nitrogen gas. The contact lens and the plate in the state of immersing in the aqueous solution were irradiated with ultraviolet-ray (wavelength: 360 nm) at an illuminance of 1.5 mW/cm$^2$ at room temperature for 10 minutes, and graft polymerization was carried out. After graft polymerization was finished, the contact lens and the plate were picked up from the aqueous solution and washed in distilled water. Furthermore, the contact lens and the plate were extracted with distilled water by using Soxhlet's extractor for 16 hours. As a result, non-reacted residual components were removed from the surface of the contact lens and the surface of the plate.

Then, the contact lens and the plate were hydrated with physiological saline to give hydrated silicone hydrogels as test pieces. Properties of the test pieces were examined in the same manner as in EXAMPLE 1, and elemental analysis of the test piece (plate) was carried out in the same manner as in EXAMPLE 1. The results are shown in TABLE 1 and TABLE 2.

Comparative Example 1

The same contact lens and the same plate as in EXAMPLE 1 were immersed in physiological saline and boiled for 1 hour to give test pieces. Properties of the test pieces were examined in the same manner as in EXAMPLE 1, and elemental analysis of the test piece (plate) was carried out in the same manner as in EXAMPLE 1. The results are shown in TABLE 1 and TABLE 2.

Comparative Example 2

The same contact lens and the same plate as in EXAMPLE 1 were set in the same discharge apparatus as in EXAMPLE 1. Plasma discharge treatment was carried out under the same condition as in EXAMPLE 1 except that plasma discharge time was changed from 10 minutes in EXAMPLE 1 to 3 minutes. After that, the contact lens and the plate were stored for at least 10 minutes under an atmosphere of air. As a result, peroxides (peroxide groups) generated on the surface of the contact lens and the surface of the plate.

Then, the contact lens and the plate were immersed in physiological saline and were boiled for 1 hour to give test pieces. Properties of the test pieces were examined in the same manner as in EXAMPLE 1, and elemental analysis of the test piece (plate) was carried out in the same manner as in EXAMPLE 1. The results are shown in TABLE 1 and TABLE 2.

Comparative Example 3

The same contact lens and the same plate as in EXAMPLE 1 were set in the same discharge apparatus as in EXAMPLE 1. Plasma discharge treatment was carried out under the same condition as in EXAMPLE 1. After that, the contact lens and the plate were stored for at least 10 minutes under an atmosphere of oxygen gas. As a result, peroxides (peroxide groups) generated on the surface of the contact lens and the surface of the plate.

Then, as the hydrophilic monomer-mixture solution, 3.0 mol/L aqueous solution of SAMA was prepared. The contact lens and the plate were immersed in this aqueous solution, and were aerated with nitrogen gas. Graft polymerization was carried out to the contact lens and the plate in the state of immersing in the aqueous solution at 60° C. for 6 hours. After graft polymerization was finished, the contact lens and the plate were picked up from the aqueous solution and washed in distilled water. Furthermore, the contact lens and the plate were extracted with distilled water by using Soxhlet's extractor for 16 hours. As a result, non-reacted residual components were removed from the surface of the contact lens and the surface of the plate.

Then, the contact lens and the plate were hydrated with physiological saline to give hydrated silicone hydrogels as test pieces. Properties of the test pieces were examined in the same manner as in EXAMPLE 1. The results are shown in TABLE 1 and TABLE 2.

The test pieces in Comparative Example 3 were deformed.

Comparative Example 4

The same contact lens and the same plate as in EXAMPLE 1 were set in the same discharge apparatus as in EXAMPLE 1. Plasma discharge treatment was carried out under the same condition as in EXAMPLE 1. After that, the contact lens and the plate were stored for at least 10 minutes under an atmosphere of oxygen gas. As a result, peroxides (peroxide groups) generated on the surface of the contact lens and the surface of the plate.

Then, 3.0 mol/L aqueous solution of 2-hydroxyethyl methacrylate as the hydrophilic monomer was prepared. The contact lens and the plate were immersed in this aqueous solution, and were aerated with nitrogen gas. The contact lens and the plate in the state of immersing in the aqueous solution were irradiated with ultraviolet-ray (wavelength: 360 nm) at an illuminance of 1.5 mW/cm$^2$ at room temperature for 10 minutes, and graft polymerization was carried out. After graft polymerization was finished, the contact lens and the plate were picked up from the aqueous solution and washed in distilled water. Furthermore, the contact lens and the plate were extracted with distilled water by using Soxhlet's extractor for 16 hours. As a result, non-reacted residual components were removed from the surface of the contact lens and the surface of the plate.

Then, the contact lens and the plate were hydrated with physiological saline to give hydrated silicone hydrogels as test pieces. Properties of the test pieces were examined in the same manner as in EXAMPLE 1. The results are shown in TABLE 1 and TABLE 2.

TABLE 1

| | | | | | | | Property of test piece | | |
| --- | --- | --- | --- | --- | --- | --- | --- | --- | --- |
| | | | | | | | | Adhesion resistance of lipid and protein | |
| | | Trans-parency | Surface wettability to water | Surface lubricity | Water content (% by weight) | Refractive index (-) | Oxygen permeability ($DK_{O_2}$) | Adhering lipid amount (mg/cm$^2$) | Adhering protein amount (μg/cm$^2$) | Graft weight (mg/mm$^2$) |
| Example No. | | | | | | | | | | |
| 1 | | ◯ | ◯ | ◯ | 31 | 1.424 | 42 | 0.065 | 0.98 | 12.56 |
| 2 | | ◯ | ◯ | ◯ | 30 | 1.425 | 44 | 0.089 | 1.02 | 1.97 |
| 3 | | ◯ | ◯ | ◯ | 30 | 1.425 | 42 | 0.078 | 1.00 | 4.29 |
| 4 | | ◯ | ◯ | ◯ | 30 | 1.425 | 43 | 0.089 | 1.00 | 0.56 |
| 5 | | ◯ | ◯ | ◯ | 30 | 1.425 | 42 | 0.084 | 1.01 | 0.91 |
| 6 | | ◯ | ◯ | ◯ | 30 | 1.425 | 42 | 0.073 | 0.95 | 0.78 |

TABLE 1-continued

| | Property of test piece | | | | | | Adhesion resistance of lipid and protein | | |
|---|---|---|---|---|---|---|---|---|---|
| | Trans-parency | Surface wettability to water | Surface lubricity | Water content (% by weight) | Refractive index (−) | Oxygen permeability ($DK_{0.2}$) | Adhering lipid amount ($mg/cm^2$) | Adhering protein amount ($\mu g/cm^2$) | Graft weight ($mg/mm^2$) |
| Com. Ex. No. | | | | | | | | | |
| 1 | ○ | x | x | 29 | 1.427 | 44 | 0.126 | 1.11 | −7.10 |
| 2 | ○ | Δ | Δ | 30 | 1.426 | 44 | 0.109 | 1.11 | −6.96 |
| 3 | Δ | ○ | ○ | 39 | 1.423 | 37 | — | — | — |
| 4 | ○ | ○ | Δ | 30 | 1.425 | 39 | 0.089 | 0.90 | — |

TABLE 2

| | Property test piece | | Elemental analysis of test piece surface |
|---|---|---|---|
| | Contact angle (°) | Water retention rate (% by weight) | O/N/C/Si/S (%) (Ex. 1–4, 6, Com. Ex. 1–2) O/N/C/Si/P (%) (Ex. 5) |
| Example No. | | | |
| 1 | 20 | 59 | 30.2/5.1/49.0/14.1/1.6 |
| 2 | 21 | 52 | 23.6/5.7/56.8/13.0/1.0 |
| 3 | 21 | 56 | 34.9/4.3/44.8/14.0/2.1 |
| 4 | 21 | 52 | 33.8/3.9/47.9/13.7/0.7 |
| 5 | 22 | 54 | 31.9/4.6/49.6/13.0/0.9 |
| 6 | 21 | 52 | 32.6/4.6/48.8/13.3/0.7 |
| Com. Ex. No. | | | |
| 1 | 36 | 39 | 22.0/5.8/57.0/15.2/0.0 |
| 2 | 29 | 40 | 23.2/5.6/56.6/14.6/0.0 |
| 3 | 20 | 59 | — |
| 4 | 24 | 44 | — |

From the results shown in TABLE 1 and TABLE 2, it can be understood that all test pieces prepared in accordance with the process of the present invention in EXAMPLES 1 to 6, are excellent in transparency, surface wettability to water, surface lubricity and oxygen permeability, and have high water retention, suitable water content and high refractive index, and are excellent in hydrophilic property because of small contact angle. In addition, it can be understood that all test pieces in EXAMPLES 1 to 6 are excellent in adhesion resistance of lipid and protein because of small adhering lipid amount and small adhering protein amount.

To the contrary, it can be understood that the test pieces in Comparative Examples 1 to 4, prepared in accordance with the process lacking even only one step of Step (1), Step (2) and Step (3) defined in the process of the present invention, cannot be satisfied with the above excellent properties exhibited by the test pieces in EXAMPLES 1 to 6, at the same time.

EXAMPLE 7
[Graft Polymerization to Hydrophobic Silicone]

As a monomer mixture, 46 parts by weight of tris(trimethylsiloxy)silylstyrene, 54 parts by weight of 2,2,2,2',2',2'-hexafluoroisopropyl methacrylate, 6 parts by weight of N-vinyl-2-pyrrolidone, 4 parts by weight of methacrylic acid, 6 parts by weight of vinylbenzyl methacrylate and 1 part by weight of EDMA were used. The monomer mixture was polymerized in accordance with a usual polymerization method to give a copolymer. Then, a contact lens (diameter: 8.8 mm, thickness: 0.15 mm) and a plate (diameter: 10.0 mm, thickness: 0.2 mm) were made of the copolymer. The contact lens and the plate were set in the same discharge apparatus as in EXAMPLE 1. After the pressure in a chamber of the discharge apparatus was reduced to about 2.66 Pa, plasma discharge treatment was carried out for 10 minutes under an atmosphere of oxygen gas of about 13.3 Pa (frequency: 13.56 MHz, high frequency power: 50 W). After that, the contact lens and the plate were stored for at least 10 minutes under an atmosphere of oxygen gas. As a result, peroxides (peroxide groups) generated on the surface of the contact lens and the surface of the plate.

Then, as the hydrophilic monomer-mixture solution, 3.0 mol/L aqueous solution of SAMA was prepared. The contact lens and the plate were immersed in this aqueous solution, and were aerated with nitrogen gas. The contact lens and the plate in the state of immersing in the aqueous solution were irradiated with ultraviolet-ray (wavelength: 360 nm) at an illuminance of 1.5 $mW/cm^2$ at room temperature for 10 minutes, and graft polymerization was carried out. After graft polymerization was finished, the contact lens and the plate were picked up from the aqueous solution and washed in distilled water. Furthermore, the contact lens and the plate were washed with washing solution containing a surfactant (trade name: Menicon $O_2$ care, made by Menicon Co., Ltd.) to give test pieces.

Transparency, surface wettability to water, oxygen permeability, adhesion resistance of lipid and contact angle of the test pieces were examined in the same manner as in EXAMPLE 1, and elemental analysis of the test piece (plate) was carried out in the same manner as in EXAMPLE 1. The results are shown in TABLE 3.

Comparative Example 5

The same contact lens and the same plate as in EXAMPLE 7 were immersed in physiological saline to give test pieces. Properties of the test pieces were examined in the same manner as in EXAMPLE 7, and elemental analysis of the test piece (plate) was carried out in the same manner as in EXAMPLE 7. The results are shown in TABLE 3.

Comparative Example 6

The same contact lens and the same plate as in EXAMPLE 7 were set in the same discharge apparatus as in EXAMPLE 1. Plasma discharge treatment was carried out under the same condition as in EXAMPLE 7 except that plasma discharge time was changed from 10 minutes in EXAMPLE 7 to 2 minutes and that high frequency power was changed from 50 W in EXAMPLE 7 to 40 W. After that, the contact lens and the plate were stored for at least 10 minutes under an atmosphere of air. As a result, peroxides (peroxide groups) generated on the surface of the contact lens and the surface of the plate.

Then, the contact lens and the plate were immersed in physiological saline to give test pieces. Properties of the test pieces were examined in the same manner as in EXAMPLE 7. The results are shown in TABLE 3.

In addition to the ingredients used in the Examples, other ingredients can be used in the Examples as set forth in the specification to obtain substantially the same results.

What is claimed is:

1. A process for preparing an ocular lens material having hydrophilic surface, characterized by comprising the steps of (1) irradiating the surface of an ocular lens material with high-frequency plasma or excimer ultraviolet-ray; (2) contacting the surface of the ocular lens material, which is treated in accordance with said step (1), with a hydrophilic monomer-mixture solution containing at least one zwitterionic group-containing compound; and (3) irradiating the surface of the ocular lens material, which is in the state of contacting with the hydrophilic monomer-mixture solution in said step (2), with ultraviolet-ray having a wavelength of 250 to 500 nm and then, graft polymerizing said zwitterionic group-containing compound to the surface of the ocular lens material and then, forming a surface layer.

2. The process of claim 1, wherein the surface of the ocular lens material, which is treated in accordance with the step (1), is contacted with the hydrophilic monomer-mixture solution by immersing the ocular lens material in the hydrophilic monomer-mixture solution in the step (2).

3. The process of claim 1, wherein the amount of the zwitterionic group-containing compound in the hydrophilic monomer-mixture solution is 0.01 to 40 mol/L.

4. The process of claim 1, wherein the hydrophilic monomer-mixture solution essentially contains water and/or an organic solvent, and further contains at least one selected from a hydrophilic monomer other than the zwitterionic group-containing compound and a crosslinkable monomer.

5. The process of claim 4, wherein the amount of the hydrophilic monomer other than the zwitterionic group-

TABLE 3

| | Property of test piece | | | | | |
|---|---|---|---|---|---|---|
| | Transparency | Surface wettability to water | Oxygen permeability ($DK_{0.2}$) | Adhesion resistance of lipid (Adhering lipid amount (mg/cm$^2$)) | Contact angle (°) | Elemental analysis of test piece surface O/N/C/Si/F/S (%) |
| Example No. | | | | | | |
| 7 | ○ | ○ | 75 | 0.121 | 15 | 22.2/1.4/55.7/6.2/13.8/0.7 |
| Com. Ex. No. | | | | | | |
| 5 | ○ | X | 77 | 0.234 | 75 | 14.7/1.6/57.5/7.5/18.7/0.0 |
| 6 | ○ | Δ | 78 | 0.198 | 15 | — |

From the results shown in TABLE 3, it can be understood that all test pieces prepared in accordance with the process of the present invention in EXAMPLE 7, are excellent in transparency, surface wettability to water, oxygen permeability and hydrophilic property because of small contact angle. In addition, it can be understood that all test pieces in EXAMPLE 7 are excellent in adhesion resistance of lipid because of small adhering lipid amount in spite of hydrophobic material.

To the contrary, it can be understood that the test pieces in Comparative Examples 5 to 6, prepared in accordance with the process not comprising Step (1), Step (2) and Step (3) defined in the process of the present invention, cannot be satisfied with the above excellent properties exhibited by the test pieces in EXAMPLE 7, at the same time.

containing compound in the hydrophilic monomer-mixture solution is 0.01 to 40 mol/L.

6. The process of claim 4, wherein the amount of the crosslinkable monomer in the hydrophilic monomer-mixture solution is 0.01 to 20 parts by weight based on 100 parts by weight of the total amount of the zwitterionic group-containing compound and the hydrophilic monomer other than the zwitterionic group-containing compound, or 100 parts by weight of the zwitterionic group-containing compound.

7. The process of claim 4, wherein the hydrophilic monomer-mixture solution further contains a chain transfer agent represented by the formula (V):

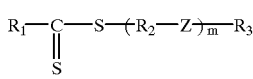

(V)

in which $R_1$ is hydrogen atom, a linear, branched or cyclic aliphatic hydrocarbon group having 1 to 12 carbon atoms, or a linear or branched aliphatic hydrocarbon group having 6 to 24 carbon atoms and containing aromatic hydrocarbon group having 6 to 12 carbon atoms; $R_2$ is a linear, branched or cyclic aliphatic hydrocarbon group having 1 to 12 carbon atoms; $R_3$ is hydrogen atom, a linear, branched or cyclic aliphatic hydrocarbon group having 1 to 12 carbon atoms, a linear or branched aliphatic hydrocarbon group having 6 to 24 carbon atoms and containing aromatic hydrocarbon group having 6 to 12 carbon atoms, or cyano group; Z is oxygen atom, —COO— group, —OOC— group, —($CH_2CH_2O$)$_l$— group (in which l is an integer of 1 to 12), or direct bond; and m is 0 or an integer of 1 to 10.

8. The process of claim 7, wherein the chain transfer agent is at least one selected from benzyl thiobenzoate, 1-phenylethyl dithiobenzoate, 2-phenyl-2-propinyl dithiobenzoate, 1-acetoxyethyl dithiobenzoate, benzyl dithioacetate, t-butyl dithiobenzoate and 2-cyano-2-propinyl dithiobenzoate.

9. The process of claim 7, wherein a residual group on a polymer chain terminal derived from the chain transfer agent, which generates after graft polymerization in the step (3), is removed or converted.

10. The process of claim 1, wherein the surface of the ocular lens material is irradiated with high-frequency plasma under an atmosphere of oxygen gas.

11. The process of claim 1, wherein the surface of the ocular lens material is irradiated with high-frequency plasma under atmospheric pressure.

12. The process of claim 1, wherein a step of (4) removing a non-reacted residual component with at least one selected from water and an organic solvent from the surface layer of the ocular lens material, which is formed in the step (3) is further contained.

13. The process of claim 1, wherein the zwitterionic group-containing compound is at least one compound selected from a compound (I) represented by the formula (I):

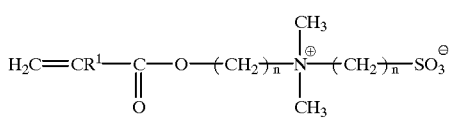

(I)

in which $R^1$ is hydrogen atom or methyl group, and n is an integer of 1 to 10;

a compound (II) represented by the formula (II):

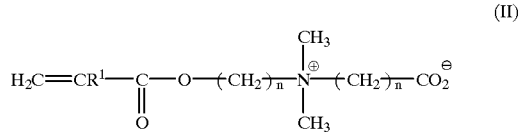

(II)

in which $R^1$ is hydrogen atom or methyl group, and n is an integer of 1 to 10;

a compound (III) represented by the formula (III):

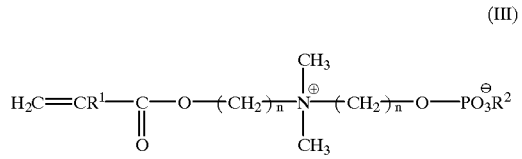

(III)

in which $R^1$ is hydrogen atom or methyl group, $R^2$ is a hydrocarbon group having 1 to 6 carbon atoms, and n is an integer of 1 to 10; and a compound (IV) represented by the formula (IV):

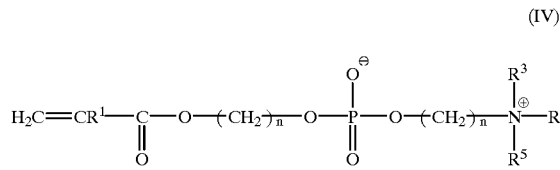

(IV)

in which $R^1$ is hydrogen atom or methyl group, each of $R^3$, $R^4$ and $R^5$ is independently a hydrocarbon group having 1 or 2 carbon atoms, and n is an integer of 1 to 10.

14. The process of claim 1, wherein the zwitterionic group-containing compound is dimethyl(3-sulfopropyl)(2-methacryloyloxyethyl) ammonium betaine.

15. The process of claim 1, wherein the zwitterionic group-containing compound is 2-methacryloyloxyethyl phosphorylcholine.

16. The process of claim 1, wherein the ocular lens material comprises a copolymer prepared by polymerizing a monomer mixture containing at least one selected from a silicon-containing monomer and a fluorine-containing monomer.

17. An ocular lens material having hydrophilic surface, prepared by the process of claim 1.

* * * * *